United States Patent

Oppelt et al.

[11] 3,992,434
[45] Nov. 16, 1976

[54] ETHANOL- AND SUBSTITUTED ETHANOLAMIDES OF HINDERED 3,5-DIALKYL-4-HYDROXYBENZOIC ACIDS

[75] Inventors: John Christian Oppelt, Somerville; Peter Vincent Susi, Middlesex, both of N.J.

[73] Assignee: American Cyanamid Company, Stamford, Conn.

[22] Filed: Dec. 30, 1974

[21] Appl. No.: 537,155

[52] U.S. Cl. .................. 260/473 S; 260/45.85 A; 260/45.9 NC; 260/559 R
[51] Int. Cl.² .................. C07C 9/78; C07C 103/26
[58] Field of Search .................. 260/473 S, 559 R

[56] References Cited
UNITED STATES PATENTS

| | | | |
|---|---|---|---|
| 3,027,301 | 3/1962 | Freedman et al. | 260/559 R |
| 3,432,550 | 3/1969 | Garzin | 260/559 R |
| 3,880,910 | 4/1975 | Spivack | 260/473 S |
| 3,907,862 | 9/1975 | Dexter et al. | 260/559 R |

*Primary Examiner*—Paul J. Killos
*Attorney, Agent, or Firm*—Philip Mintz

[57] ABSTRACT

Compounds of the formula:

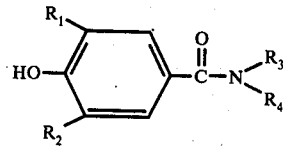

wherein $R_1$ and $R_2$ are each branch-chain alkyl of 3 to 8 carbon atoms, $R_3$ is —$CH_2CH_2OZ$ wherein Z is hydrogen or

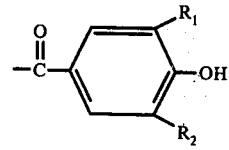

and $R_4$ is hydrogen or $R_3$ are useful as light stabilizers in polyolefins. They may be prepared (a) by reacting the 3,5-di-alkyl-4-hydroxybenzoyl chloride with the appropriate amine in the presence of an acid acceptor or (b) by reacting the corresponding benzoic acid with the appropriate amine in the presence of a carbodiimide as dehydrating agent.

4 Claims, No Drawings

ETHANOL- AND SUBSTITUTED ETHANOLAMIDES OF HINDERED 3,5-DIALKYL-4-HYDROXYBENZOIC ACIDS

This invention relates to stabilizing polyolefins against the deteriorating effects of light by the use of certain amides of hindered 3,5-dialkyl-4-hydroxybenzoic acid.

As is well known, polyolefins such as polypropylene tend to deteriorate from the effects of light, especially ultraviolet light. This deterioration generally manifests itself as a loss of tensile strength and loss of flexibility of the polymer. In accordance with the present invention, we have discovered that certain amides of hindered 3,5-dialkyl-4-hydroxybenzoic acid can significantly retard or inhibit such deterioration.

The amides of hindered 3,5-dialkyl-4-hydroxybenzoic acid useful for the practice of the present invention include those having the formula:

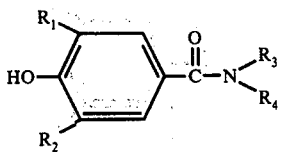

wherein $R_1$ and $R_2$ are each branched-chain alkyl of 3 to 8 carbon atoms, $R_3$ is $-CH_2CH_2OZ$ wherein Z is hydrogen or

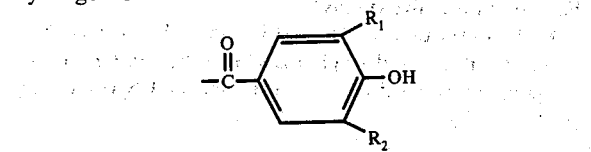

and $R_4$ is hydrogen or $R_3$. Illustrative of the branched-chain alkyl moieties from which $R_1$ and $R_2$ may be separately selected are isopropyl, t-butyl, iso-hexyl, cyclohexyl, 2-ethylhexyl, t-octyl, etc. It is preferred for both $R_1$ and $R_2$ to be t-butyl because of the commercial availability of 3,5-di-t-butyl-4-hydroxybenzoic acid, an intermediate from which the amides of the present invention can be prepared.

These new compounds can be prepared in several ways from 3,5-dialkyl-4-hydroxybenzoic acid or its acid chloride. Briefly, one such preparation involves the reaction of the acid chloride with the appropriate amine in the presence of an acid acceptor. Another such preparation involves the condensation of the acid with the appropriate amine in the presence of a carbodiimide as dehydrating agent. Preparations of these new compounds by both these procedures are illustrated in the following examples.

The 3,5-dialkyl-4-hydroxybenzoic acid chloride can be prepared by reacting the corresponding benzoic acid with thionyl chloride in the presence of a catalyst, such as pyridine. The benzoic acid may be purchased (especially the 3,5-di-t-butyl-4-hydroxybenzoic acid) or may be prepared by oxidation of the corresponding aldehyde; see Yohe et al., J. Org. Chem., 1289 (1956) as explained in U.S. Pat. No. 3,206,431 col. 3, lines 32-35. The acid and acid chloride are also described in U.S. Pat. No. 3,330,859 (Examples 3, 5, and 6).

The compounds of this invention are useful for protecting polyolefins, such as polypropylene and polyethylene, against the deteriorative effects of ultraviolet light when used in amounts of about 0.1 to about 2.0 percent by weight, preferably of about 0.2 to about 1.0 percent by weight, on weight of polymer. These compounds may be incorporated into the polyolefin by any of the standard techniques used in industry, such as by milling, extrusion, swelling into the polymer, etc. Other additives, such as processing antioxidants, secondary stabilizers, pigments, dyes, flame retardants, lubricants, plasticizers, etc. may also be included in the polyolefin for their usual purposes.

For further illustration of this invention, reference should be made to the following examples.

EXAMPLE 1

To a solution of 25 milliliters of diethanolamine in 50 milliliters of dry tetrahydrofuran was added a solution of 6.7 grams of 3,5-di-t-butyl-4-hydroxybenzoyl chloride in benzene. The resulting mixture was stirred overnight at room temperature, the excess diethanolaimne was decanted; the benzene-tetrahydrofuran layer was removed, washed with water, dried, and evaporated to yield an oil, which, after crystallization with aqueous ethanol yielded a white solid. Small amounts of by-product compounds of Examples 3 and 4 were removed by fractional recrystallization to yield N,N-dihydroxyethyl-3,5-di-t-butyl-4-hydroxybenzamide; melting point 147°-150° C.

EXAMPLE 2

Testing in Polypropylene

The compound of Example 1 (0.5% by weight) was milled into unstabilized polypropylene along with 0.2% by weight of a thermal antioxidant, 2,4,6-tri-t-butylphenol. The milled composition was then compression molded into a film 4 mils thick. The compression molded film, and a control film identically prepared except without the compound of Example 1, were exposed in a Fade-Ometer until they failed. The samples were considered as having failed when the carbonyl content in the film, as measured in the infra-red spectrum, reached 0.1%. This carbonyl content generally results in film embrittlement. The test sample lasted 1,550 hours, about 2.8 times as long as the control.

EXAMPLE 3

One mole of 3,5-di-t-butyl-4-hydroxybenzoyl chloride in benzene was reacted with two moles of diethanolamine in benzene to produce N,N-bis(3',5'-di-t-butyl-4'-hydroxybenzoyloxyethyl) 3,5-di-t-butyl-4-hydroxybenzamide; melting point 200°-202° C. When tested by the procedure of Example 2, the sample containing this compound lasted 1,300 hours, about 2.4 times as long as the control.

EXAMPLE 3'

Three moles 3,5-di-t-butyl-4-hydroxybenzoyl chloride and 1 mole diethanolamine in benzene are stirred at room temperature for 16 hours. The reaction mixture is poured into water, the benzene layer is separated and the benzene evaporated under reduced pressure to provide N,N-bis(3',5'-di-tert.-butyl-4'-hydroxybenzoyloxyethyl)-3,5-di-tert.butyl-4-hydroxybenzamide as a white solid.

EXAMPLE 4

To a cold (5° C.) solution of 3 moles of diethanolamine in tetrahydrofuran was added dropwise a solution of 3,5-di-t-butyl-4-hydroxybenzoyl chloride in benzene. The reaction mixture was stirred for about 1 hour, washed with water, separating the benzene layer from the aqueous layer. The benzene solution was evaporated to yield an oil, which, after crystallization with aqueous ethanol, yielded a white solid. Small amounts of by-product compounds of Examples 1 and 3 were removed by fractional crystallization to yield N-hydroxyethyl-N-(3',5'-di-t-butyl-4'-hydroxybenzoyloxyethyl)-3,5-di-t-butyl-4-hydroxybenzamide; melting point 174°–178° C. When tested by the procedure of Example 2, the sample containing this compound lasted 1,200 hours, about 2.2 times as long as the control.

EXAMPLE 5

To a stirred solution of 25 grams (0.1 mole) of 3,5-di-t-butyl-4-hydroxybenzoic acid and 29.3 grams (0.1 mole) of N-(3,5-di-t-butyl-4'hydroxybenzoyloxyethyl-)amine in 100 milliliters of dry tetrahydrofuran was added dropwise a solution of 20.6 grams (0.1 mole) of dicyclohexylcarbodiimide in 75 milliliters of dry tetrahydrofuran. The mixture was stirred for several hours and the white solid (dicyclohexyl urea) was filtered off and discarded. Evaporation of the filtrate gave a product which was recrystallized from 1:1 benzene-hexane to give N-(3',5'di-t-butyl-4'-hydroxybenzoyloxyethyl)-3,5-di-t-butyl-4-hydroxybenzamide; melting point 185°–187° C. When tested by the procedure of Example 2, the sample containing this compound lasted 1,000 hours, about 3.3 times as long as the control.

EXAMPLES 6–8

When tested by the procedure of Example 2, corresponding amides prepared from aromatic amines were found to be ineffective, in that the time to failure did not significantly exceed the time to failure of the control. Amides tested were (Example 6) N-o-tolyl-3,5-di-t-butyl-4-hydroxybenzamide; (Example 7) N-p-tolyl-3,5-di-t-butyl-4-hydroxybenzamide; and (Example 8) N-(2-hydroxyphenyl)-3,5-di-t-butyl-4-hydroxybenzamide. Accordingly, these compounds are outside the scope of the present invention.

What is claimed is:

1. A compound of the formula:

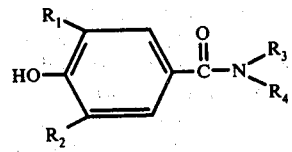

wherein $R_1$ and $R_2$ are each branch-chain alkyl of 3 to 8 carbon atoms, $R_3$ is —$CH_2CH_2OZ$ wherein Z is hydrogen or

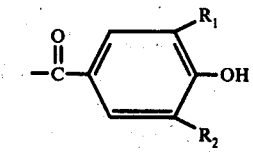

and $R_4$ is hydrogen or $R_3$.

2. A compound as defined in claim 1 wherein $R_1$ and $R_2$ are each t-butyl.

3. A compound as defined in claim 2 wherein $R_3$ and $R_4$ are each hydroxyethyl.

4. A compound as defined in claim 2 wherein $R_3$ is 3,5-di-t-butyl-4-hydroxybenzoyloxyethyl and $R_4$ is hydrogen, hydroxyethyl, or 3,5-di-t-butyl-4-hydroxybenzoyloxyethyl.

* * * * *